United States Patent [19]

Scarborough

[11] Patent Number: 5,744,584
[45] Date of Patent: Apr. 28, 1998

[54] ANTITHROMBOSIS AGENTS

[75] Inventor: Robert M. Scarborough, Belmont, Calif.

[73] Assignee: COR Therapeutics, Inc., South San Francisco, Calif.

[21] Appl. No.: 481,676

[22] Filed: Jun. 7, 1995

Related U.S. Application Data

[62] Division of Ser. No. 294,859, Aug. 29, 1994, Pat. No. 5,679,542, which is a division of Ser. No. 614,443, Nov. 16, 1990, Pat. No. 5,342,830.

[51] Int. Cl.[6] .......................... C07K 16/18; G01N 33/53
[52] U.S. Cl. .................. 530/388.1; 435/7.21; 436/518; 436/536; 530/389.1
[58] Field of Search ............... 435/7.21; 530/388.1, 530/389.1; 436/518, 536

[56] References Cited

U.S. PATENT DOCUMENTS

| | | | |
|---|---|---|---|
| 3,819,605 | 6/1974 | Holleman et al. | 530/417 |
| 4,350,625 | 9/1982 | Abe | 530/856 |
| 5,066,592 | 11/1991 | Huang et al. | 530/856 |
| 5,196,193 | 3/1993 | Carroll | 530/389.1 |
| 5,336,667 | 8/1994 | Kirby et al. | 514/12 |

FOREIGN PATENT DOCUMENTS

| | | |
|---|---|---|
| 87/73715 | 12/1987 | Australia. |
| B-33299/89 | 2/1990 | Australia. |
| 0 317 278 | 5/1989 | European Pat. Off.. |
| A-0 382 451 | 8/1990 | European Pat. Off.. |
| 53-139711 | 12/1978 | Japan. |
| WO 89/04166 | 5/1989 | WIPO. |
| WO 90/00178 | 1/1990 | WIPO. |
| WO 90/15620 | 12/1990 | WIPO. |

OTHER PUBLICATIONS

Becker et al., *Blood*, (1989), vol. 74, pp. 690–694.
Bellinger et al., *Proc. Natl. Acad. Sci. USA* (1987), vol. 84, pp. 8100–8104.
Cadroy et al., *Circulation* (1989), vol. 80:Suppl. II–24.
Coller et al., *Blood*, (1983), vol. 61, p. 69.
Fressinaud et al., *J. Lab. Clin. Med.* (1988), vol. 112, pp. 58–67.
Geratz et al., *Thromb. Haemostasis*, (1978), vol. 39, p. 411.
Kirby, *Thromb. Haemostasis*, (1975) vol. 34, p. 770.
Phillips et al., *Blood*, (1988), vol. 72, pp. 1898–1903.
Ruan et al., *Brit. Journal Haemotol.*, (1981), vol. 49, p. 511.
Stein et al., *Circulation*, (1989) vol. 80, pp. 1501–1513.
Strony et al., *Circulation*, (1989), vol. 80, pp. II-23 (Abstract).
Vincente et al., *J. Biol. Chem.* (1990), vol. 265, pp. 274–280.
Andrews, et al., *Biochemistry*, 1989; vol. 28, pp. 8317–8326: "Purification of Botrocetrin from *Bothrops jararaca* Venom . . . ".
Atoda et al., *The Journal of Biological Chemistry*, Aug. 13, 1991, vol. 266(23), pp. 14903–14911, "The Primary Structure of Coagulation Factor IX/Factor X–binding . . . ".
Daoud et al., *Thrombosis Research*, 1986, vol. 42, pp. 55–62: "Isolation and Characterization of an Anticoagulant Protease . . . ".
Dennis et al., *PNAS*, Apr. 1989, vol. 87, pp. 2471–2475: "Platelet Glycoprotein IIb–IIa Protein Antagonists from Snake Venoms . . . ".
el–Asmar et al., *Medline* 1986, No. 87179104, "Coagulant Component in *Cerastes cerastes* (Egyptian Sand Viper) Venom.".
Soslau et al., *Medline*, 1988, No. 88134252, "*Cerastes cerastes* (Egyptian Sand Viper) Venom Induced Platelet . . . ".
Verheij et al., *Eur. J. Biochem.*, 1980, vol. 112, pp. 25–32: "Correlation of Enzymatic Activity and Anticoagulant Properties . . . ".

*Primary Examiner*—David Saunders
*Attorney, Agent, or Firm*—Morgan, Lewis & Bockius LLP

[57] ABSTRACT

Platelet antiadhesives (PAA) which are useful as antithrombotics are obtainable from snake venoms which have been identified using an assay which measures the ability of the venom to inhibit ristocetin- or botrocetin-induced agglutination of platelets in the presence of von Willebrand Factor. The antiadhesives of the invention are 20–24 kd dimers of smaller peptides, or effective portions thereof. Antibodies to these antiadhesives are also prepared and are useful in assays for PAA and for screening expression libraries for PAA encoding DNA.

20 Claims, 10 Drawing Sheets

Reduced

Non-reduced

FIG. 6A

CHH-B α chain

```
Asp Leu Glu Cys Pro Ser Gly Trp Ser Ser Tyr Asp Arg Tyr Cys Tyr Lys Pro Phe
 1                       5                      10                      15
Lys Gln Glu Met Thr Trp Ala Asp Ala Glu Arg Phe Cys Ser Glu Gln Ala Lys Gly
20                      25                      30                35
Arg His Leu Leu Ser Val Glu Thr Ala Leu Glu Ala Ser Phe Val Asp Asn Val Leu
40                      45                      50                      55
Tyr Ala Asn Lys Glu Tyr Leu Thr Arg Tyr Ile Trp Ile Gly Leu Arg Val Gln Asn
             60                      65                      70                75
Lys Gly Gln Pro Cys Ser Ser Ile Tyr Ser Glu Asn Leu Val Asp Pro Phe Glu Cys
             80                      85                      90                95
Phe Met Val Ser Arg Asp Thr Arg Leu Arg Glu Trp Phe Lys Val Asp Cys Glu Gln
            100                     105                     110
Gln His Ser Phe Ile Cys Lys Phe Thr Arg Pro Arg Arg
            115                     120                     125
```

FIG. 6B

CHH-B β chain

Asp Cys Pro Ser Asp Trp Ser Ser Tyr Glu Gly His Cys Tyr Arg Val Phe Gln Gln
1                         5                         10                        15

Glu Met Thr Trp Asp Asp Ala Glu Lys Phe Cys Thr Gln Gln His Thr Gly Gly His
20                        25                        30                        35

Leu Val Ser Phe Arg Ser Ser Glu Glu Val Asp Phe Leu Val Ser Ile Leu Lys Phe
40                        45                        50                        55

Asp Leu Phe Trp Met Gly Trp Arg Asp Ile Trp Asn Glu Arg Arg Leu Gln Trp Ser
60                        65                        70                        75

Asp Gly Thr Lys Val Asn Tyr Lys Ala Trp Ser Ala Glu Pro Glu Cys Ile Val Cys
80                        85                        90                        95

Arg Ala Thr Asp Asn Gln Trp Leu Ser Thr Ser Cys Ser Lys Thr His Asn Val Val
100                       105                       110

Cys Lys Phe
115

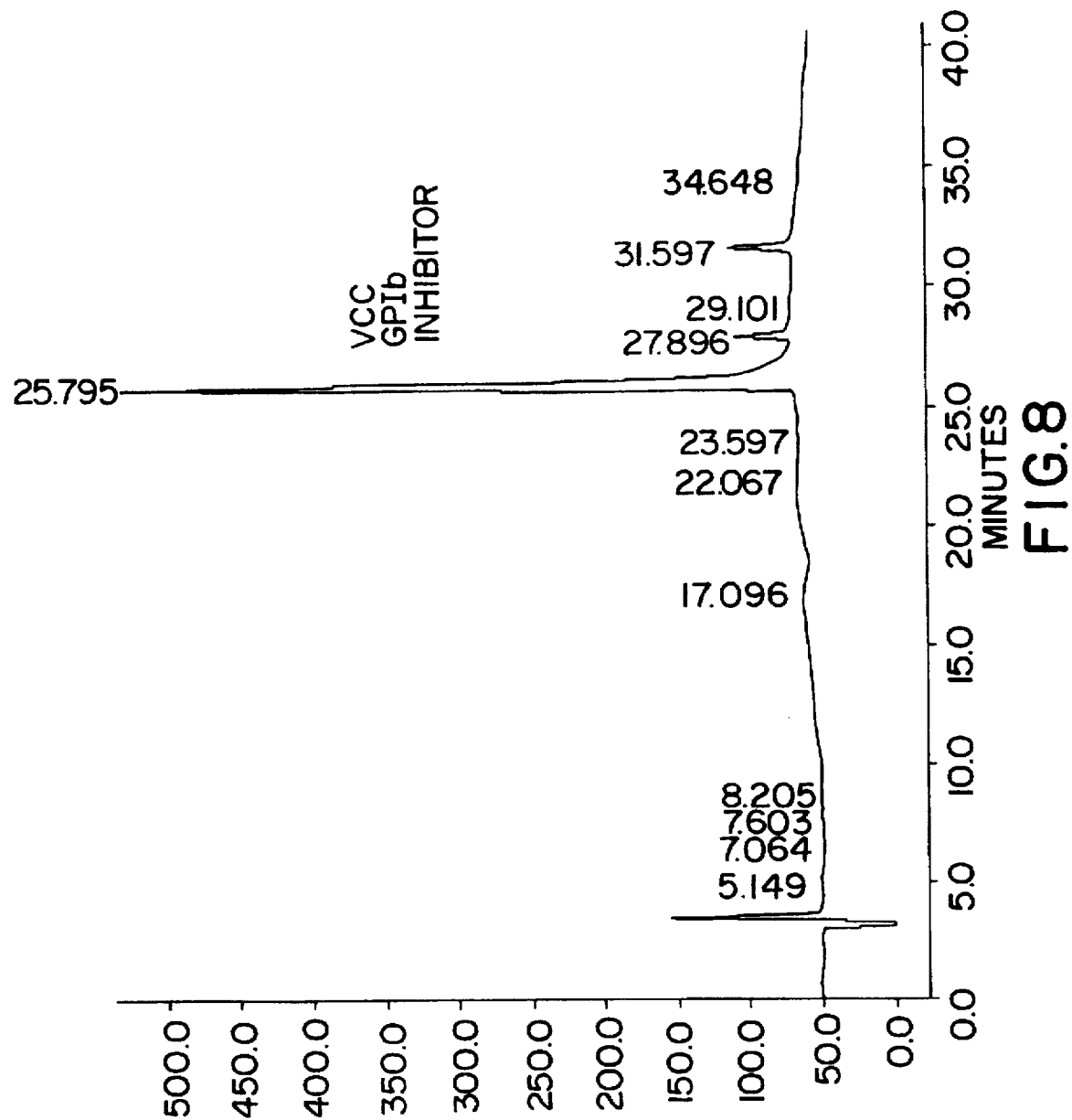

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 127 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Asp Leu Glu Cys Pro Ser Gly Trp Ser Ser Tyr Asp Arg Tyr Cys Tyr
 1               5                  10                  15
Lys Pro Phe Lys Gln Glu Met Thr Trp Ala Asp Ala Glu Arg Phe Cys
                20                  25                  30
Ser Glu Gln Ala Lys Gly Arg His Leu Leu Ser Val Glu Thr Ala Leu
                35                  40                  45
Glu Ala Ser Phe Val Asp Asn Val Leu Tyr Ala Asn Lys Glu Tyr Leu
        50                  55                  60
Thr Arg Tyr Ile Trp Ile Gly Leu Arg Val Gln Asn Lys Gly Gln Pro
65                  70                  75                  80
Cys Ser Ser Ile Tyr Ser Glu Asn Leu Val Asp Pro Phe Glu Cys Phe
                85                  90                  95
Met Val Ser Arg Asp Thr Arg Leu Arg Glu Trp Phe Lys Val Asp Cys
               100                 105                 110
Glu Gln Gln His Ser Phe Ile Cys Lys Phe Thr Arg Pro Arg Arg
               115                 120                 125
```

( 2 ) INFORMATION FOR SEQ ID NO:2:

( i ) SEQUENCE CHARACTERISTICS:
        ( A ) LENGTH: 117 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

Asp Cys Pro Ser Asp Trp Ser Ser Tyr Glu Gly His Cys Tyr Arg Val
1               5                   10                  15

Phe Gln Gln Glu Met Thr Trp Asp Asp Ala Glu Lys Phe Cys Thr Gln
            20                  25                  30

Gln His Thr Gly Gly His Leu Val Ser Phe Arg Ser Ser Glu Glu Val
        35                  40                  45

Asp Phe Leu Val Ser Ile Leu Lys Phe Asp Leu Phe Trp Met Gly Trp
    50                  55                  60

Arg Asp Ile Trp Asn Glu Arg Arg Leu Gln Trp Ser Asp Gly Thr Lys
65                  70                  75                  80

Val Asn Tyr Lys Ala Trp Ser Ala Glu Pro Glu Cys Ile Val Cys Arg
                85                  90                  95

Ala Thr Asp Asn Gln Trp Leu Ser Thr Ser Cys Ser Lys Thr His Asn
            100                 105                 110

Val Val Cys Lys Phe
            115

( 2 ) INFORMATION FOR SEQ ID NO:3:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

Leu Asp Cys Pro Leu Asp Ser Ser Xaa His Glu Glu Lys Cys Tyr Lys
1               5                   10                  15

Val Phe Phe Leu Leu Xaa Thr Trp Glu
            20                  25

( 2 ) INFORMATION FOR SEQ ID NO:4:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

Asp Gln Asp Cys Leu Pro Gly Trp Ser Tyr Tyr Glu Lys Tyr Cys Tyr
1               5                   10                  15

Lys Val Phe Glu
            20

( 2 ) INFORMATION FOR SEQ ID NO:5:

( i ) SEQUENCE CHARACTERISTICS:
        ( A ) LENGTH: 50 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

Asp Cys Pro Ser Asp Trp Ser Ser His Glu Gly His Cys Tyr Lys Val
1               5                   10                  15

Phe Asn Leu Tyr Lys Thr Trp Glu Asp Ala Glu Lys Phe Cys Thr Glu
            20                  25                  30

Gln Ala Asn Gly Gly His Leu Val Ser Ile Asp Ser Lys Lys Glu Ala
        35                  40                  45

```
           Asn  Phe
                50
```

( 2 ) INFORMATION FOR SEQ ID NO:6:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
Ala  Leu  Asn  Cys  Ala  Ser  Gly  Trp  Ser  Ala  Tyr  Asp  Gln  His  Cys  Tyr
1                   5                             10                       15

Lys  Ala  Phe  Asp  Glu  Pro  Lys  Ser  Trp  Ala  Asp  Asp  Glu  Lys  Phe
                20                       25                       30
```

( 2 ) INFORMATION FOR SEQ ID NO:7:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

```
Gly  Phe  Ser  Cys  Pro  Asn  Gly  Trp  Ser  Ser  Phe  Gly  Arg  Tyr  Cys  Tyr
1                   5                             10                       15

Lys  Pro  Ile  Glu  Pro  Leu
                20
```

ANTITHROMBOSIS AGENTS

This application is a division of application Ser. No. 08/294,859 filed 29 Aug. 1994, now U.S. Pat. No. 5,619,542, which is a division of application Ser. No. 07/614,443 filed 16 Nov. 1990 and now U.S. Pat. No. 5,342,830.

TECHNICAL FIELD

The invention relates to inhibitors of platelet adhesion. More specifically, it concerns proteins and peptides which inhibit the binding of von Willebrand Factor (vWF) to the platelet glycoprotein GPIb-IX complex thus preventing platelet-vessel wall adherence. Some of these peptides are present in snake venom.

BACKGROUND ART

Thrombosis within the cardiovascular system is believed to be the principal mechanism for vasoocclusive disorders, which are responsible for much morbidity and mortality in Western societies. Thus, antithrombotic drugs have been used extensively for treating many of these disorders (see, for example, Stein et al., *Circulation* (1989) 80:1501–1513). As with any group of drugs, however, none is entirely satisfactory for all individuals, and additions to the repertoire of possible therapeutic agents are always welcome.

The mechanism for the formation of thromboses is complex, but partially understood. An initial trauma, such as that initiated by rupture of atherosclerotic plaques or following mechanical removal of plaques during angioplasty, results in adhesion of platelets to the damaged vessel wall through platelet-to-nonplatelet interactions, and subsequent platelet aggregation (platelet-to-platelet interactions), in combination with deposition of fibrin. This sequence of events is controlled by the interaction of plasma proteins with specific platelet surface glycoprotein receptors. Since platelet adhesion is thought to be the initial response to injury, it is an especially desired target for inhibition in order to prevent or ameliorate thrombosis and/or restenosis that may be mediated by adherent platelets.

Unstimulated circulating platelets contain receptors for several adhesive proteins. Among these are laminin, which binds to VLA 2 and VLA 6, and collagen, which binds to VLA 2, GPIV, and others. The initial attachment of platelets to the subendothelium is believed to be mediated by the binding of the GPIb-IX complex residing on the platelet surface to von Willebrand Factor (vWF), which is immobilized in the vessel wall, particularly under the high shear rate conditions found at the sites of arteriovascular occlusion. The platelet GPIb-IX complex, while functional generally on resting platelets, normally does not bind plasma-borne vWF. Under normal circumstances, the arterial surface does not provide adhesive protein ligands (vWF) for platelet adherence; thus, platelet adhesion is limited to the vWF bound at the sites of vascular damage.

When the presence of bound vWF supports the adhesion of the platelets to the endothelium, the platelets become activated and are then capable of forming platelet aggregates, associated with the binding of fibrinogen (Fg) and plasma-borne vWF, through the now-activated GPIIb-IIIa receptor. It follows that substances which specifically inhibit the adhesion of the unactivated platelets through the GPIb-IX-bound vWF interaction would interrupt the formation of thromboses, especially in vessels wherein high shear stress is caused by stenoses.

The GPIb-IX complex, formed from the Ib surface membrane heterodimer ($Ib_\alpha$ and $Ib_{62}$) noncovalently complexed with GPIX, is present at a density of approximately 25,000 copies/platelet surface. The absence of this complex has been shown to be responsible for Bernard-Soulier Syndrome, a rare congenital bleeding disorder characterized by the absence of GPIb-IX complex displayed on the platelet surface and defective arterial adhesion of platelets. Defects in von Willebrand factor, such as those characterizing von Willebrand Disease also have been shown to lead to defective arterial adhesion of platelets.

Substances capable of interfering with GPIb-IX/vWF interaction are known. Kirby, Thombos, Diathes, Haemorrh. (1975) 34:770, reports that Evans' blue dye inhibits the ristocetin-induced binding of vWF to formaldehyde-fixed platelets in vitro. Geratz et al, *Thromb Haemostasis* (1978), 39:411, showed the same effect by aromatic amidino compounds. Phillips et al, *Blood* (1988) 72:1898–1903, showed that ristocetin-induced platelet agglutination as well as shear-induced platelet aggregation in platelet-rich plasma was effectively inhibited by the triphenylmethyl compound aurin tricarboxylic acid (ATA) at concentrations tenfold lower than those of other compounds previously described. ATA has also been demonstrated to be an effective inhibitor of coronary artery thrombosis in vivo (Strony et al, *Circulation* (1989) 80:II-23 (Abstract); PCT Application WO 89/04166.

Binding of vWF to GPIb-IX complex has also been inhibited by monoclonal antibodies immunoreactive with the GPIb-IX complex as disclosed by Ruan et al, *Brit J Haemotol* (1981) 49:511; and Coller et al, *Blood* (1983), 61(1):99–119). The antibodies inhibit ristocetin-induced binding of vWF to platelets. Becker et al, *Blood* (1989) 74:690–694, showed that one of these antibodies or its immunoreactive fragments block GPIb function in guinea pigs in vivo, although they exert no effect on platelet aggregation induced by ADP, collagen, or thrombin.

Monoclonal antibodies immunoreactive with human vWF block platelet adhesion to collagen at high shear rates (Fressinaud et al, *J Lab Clin Med* (1988) 11:58–67, and Cadroy et al., *Circulation* (1989) 80:Suppl. II-24). Murine monoclonal antibodies against porcine von Willebrand factor induce an antithrombotic state in normal pigs without effecting intrinsic platelet function (Bellinger et al., *Proc Natl Acad Sci* (USA) (1987) 84:8100–8104).

A proteolytic 45 kd fragment of glycocalicin (a GPIb fragment) and its derivatives inhibit binding of vWF to platelets, and these peptides can be used as antithrombotic agents, as shown in EPO Publication No. 317278. Fragments of vWF also inhibit this binding, as described in Australian Patent Application AU87/73715. Vicente et al., *J Biol Chem* (1990) 26:274–280, discloses peptides derived from GPIb which block ristocetin- and botrocetin-induced binding of vWF to platelets.

The peptides of the present invention provide alternative approaches to antithrombosis by specifically inhibiting the binding of vWF with the GPIb-IX platelet-borne complex. These are effective agents in antithrombotic therapies.

DISCLOSURE OF THE INVENTION

The invention is directed to peptide inhibitors of platelet adhesion to the subendothelium which are useful as antithrombotic agents. It has been found that a number of such proteins are present in snake venom, and methods to purify these proteins are provided. Methods for identification of those venoms which contain the desired inhibitors are also described.

Thus, in one aspect, the invention is directed to antithrombotic agents which are inhibitors of vWF/GPIb-IX interaction. More specifically these peptides appear to bind to GPIb-IX and block the binding of vWF. These antithrombotic agents are collectively called platelet antiadhesives. The platelet antiadhesives found in snake venom, as described herein, are 24–28 kd peptides consisting of two nonidentical disulfide-linked subunits of 12–14 kd each. Significant sequence homology exists between the two subunits of each of the peptide anti-adhesives.

In another aspect, the invention is directed to methods to identify biological fluids, including snake venoms, which provide the platelet antiadhesives of the invention.

In still other aspects, the invention is directed to methods to prevent or ameliorate thrombosis by the use of the platelet antiadhesives of the invention, and to pharmaceutical compositions containing these antiadhesives.

BRIEF DESCRIPTION OF THE DRAWINGS

FIG. 6A shows the amino acid sequence of the *C. h. horridus* GPIb inhibitor α chain (SEQ ID NO:8). FIG. 6B shows the amino acid sequence of the *C. h. horridus* GPIb inhibitor β chain (SEDQ ID NO:9) shows the amino acid sequences of the *C. h. horridus* GPIb inhibitor α and β chains.

FIG. 8 shows the RPLC chromatogram of purified VCC GPIb inhibitor from *Cerastes cerastes* on a $C_4$ column.

MODES OF CARRYING OUT THE INVENTION

Figure 1:
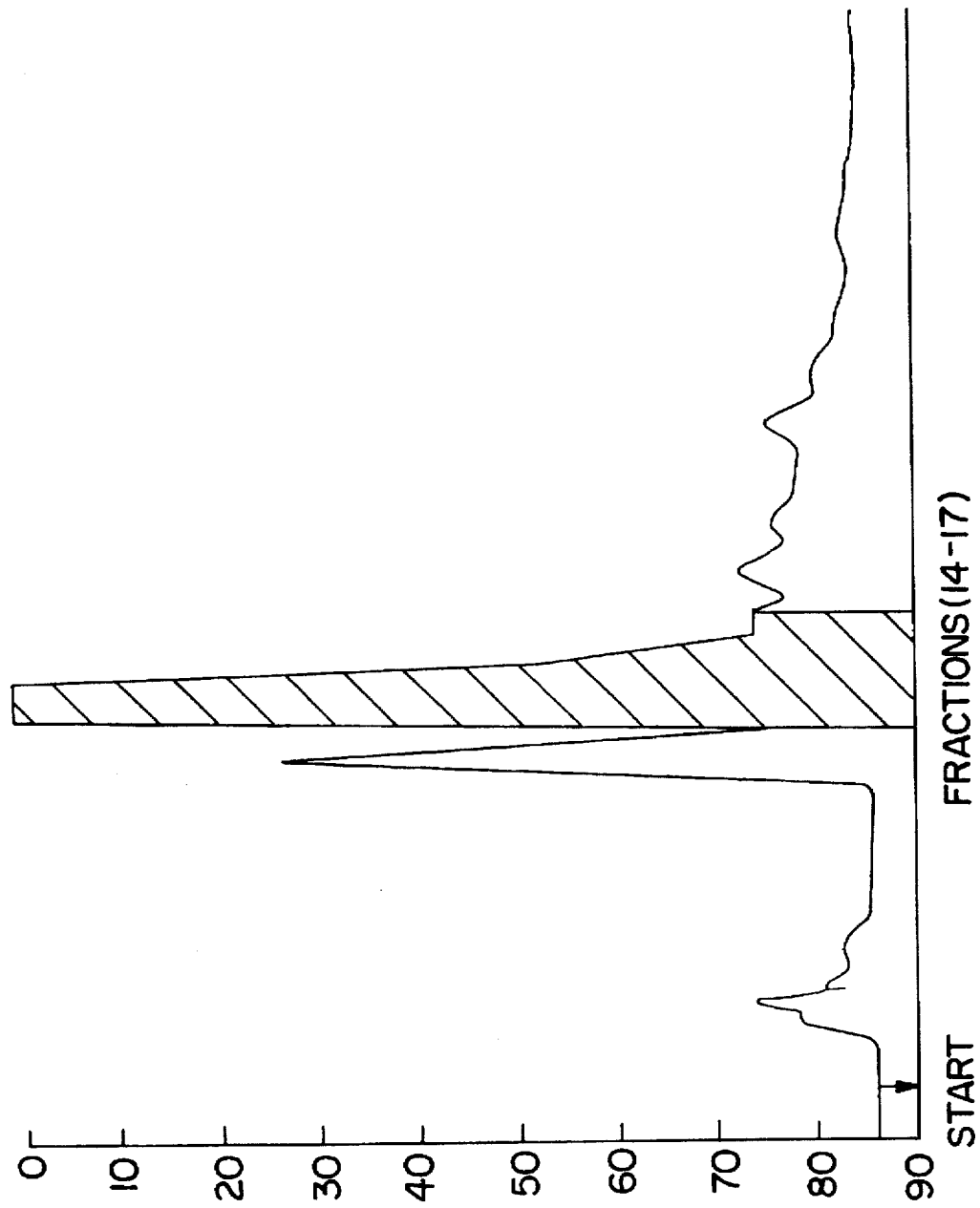
FIG. 1 shows the chromatogram of CHH GPIb inhibitor purified on CM-sepharose using $NH_4OAc$ gradient elution, monitored by absorbance at 254 nm.

The platelet antiadhesives of the invention have certain in vitro properties which relate to their behavior as antithrombotic agents. All of the antiadhesives of the invention fail to inhibit platelet aggregation induced by ADP, collagen, and thrombin; thus they are not inhibitors of Fg binding to GPIIb-IIIa and do not inhibit platelet aggregation. However, they do prevent the agglutination of unstimulated platelets in standard assays, such as those described by Allain, J. P., et al., *J Lab Clin Med* (1975) 85:318, and Read, M. S., et al., *J Clin Lab Med* (1983) 101:74. They also inhibit the binding of labeled vWF to washed platelets using a standard assay such as that of Ruggeri, C. M., et al, *J Clin Invest* (1983) 72:1–12.

The following are assays in which the platelet antiadhesives of the invention give positive results:

1) Inhibition of Ristocetin or Botrocetin Agglutination of Platelets

In this assay, formaldehyde fixed-washed platelets prepared as described by Brinkhaus, A. M., et al, *Meth Enzymol* (1989) 169:149–143, are mixed with purified vWF prepared as described by Thorell, L., et al, *Thromb Res* (1984) 35:431–450, and agglutination is initiated with either the antibiotic ristocetin or the snake venom agglutinin botrocetin. Increasing concentrations of substances to be tested for platelet antiadhesive activity are incubated with the fixed platelets in the presence of vWF for 1 minute prior to addition of the agglutination inducer. Agglutination is measured in a commercially available aggregometer such as that supplied by Chronolog Corporation (Havertown, Pa.) and is a measure of the binding of vWF to the GPIb-IX complex.

(While some samples can be tested in platelet-rich plasma (PRP) instead of the fixed platelet assay, this form of the assay is not preferred for crude materials such as snake venom, which may contain high concentrations of coagulating enzymes.)

2) Inhibition of Labeled vWF Binding to Platelets

The antiadhesives of the invention also inhibit the ristocetin- or botrocetin-induced binding of radiolabeled, biotinylated or otherwise labeled vWF to platelets. The platelets can be provided as washed platelets and the assay conducted as described by Ruggeri et al. (*J Clin Inves* (1983) 72:1–12, supra), to glycocalicin bound to ELISA plates, or to platelets or GPIX-Ib in any suitable form.

Thus, in general, the antiadhesives of the invention are positive both in assays which measure ability to inhibit platelet agglutination induced by ristocetin- or botrocetin and which measure ability to inhibit ristocetin- or botrocetin-induced vWF binding to platelets. However, they do not interfere with the binding of fibrinogen to the GPIIb-IIIa receptor.

Identification of Sources of Antiadhesives

Biological fluids, such as snake venoms, which contain the platelet antiadhesives of the invention are effectively identified using the ristocetin/botrocetin agglutination inhibition assay with fixed-washed platelets, as described above, or an assay which measures inhibition of vWF binding to GPIb-IX platelet-borne complex.

Successful candidates are subjected to purification procedures to obtain the platelet antiadhesives in isolated and purified form. While a variety of protein purification techniques can be used, such as size chromatography, ion-exchange chromatography, and reverse-phase HPLC, a typical and successful procedure is as follows:

About 10–1000 mg of crude venom in lyophilized form is reconstituted in dilute acetic acid (0.5M) and applied to a sizing column, such as Sephadex G-50, and eluted in the same solvent. After lyophilization to remove acetic acid, fractions are assayed for antiadhesive activity using the fixed-washed platelet botrocetin or ristocetin-induced agglutination assay with purified vWF, as described above.

Active fractions identified from the sizing column are then adsorbed onto carboxymethyl (CM)-sephacyl or diethylaminoethyl (DEAE)-sephacyl columns depending on the ionic charge of the antiadhesive in the snake venom, and eluted from the column using increasing ionic strength ammonium acetate buffer. Fractions from the column are again lyophilized to remove the volatile salt and assayed using the platelet agglutination assay as described above. (In some cases platelet-rich plasma (PRP) can be substituted for the fixed-washed platelets at this stage if the clotting activity present in many crude snake venoms has been removed from active fractions.)

Active fractions from the ion-exchange steps can then be purified using preparative reversed-phase liquid chromatography (RPLC) on $C_4$ RPLC columns, such as Vydac, and eluting with gradients containing acetonitrile (2–70% acetonitrile) and 0.1% TFA/$H_2O$. The slope of the gradient and flow rate are optimized using routine procedures. Active fractions are determined by the platelet agglutination assay described above, now using PRP as the platelet preparation. The active fractions are then pooled, concentrated and tested for homogeneity using analytical HPLC or SDS-PAGE.

Antiadhesives of the invention, obtainable by the foregoing or other purification methods include those from venoms selected from the group consisting of: *Agkistrodon acutus, Agkistrodon halvs blomhoffi, Agkistrodon contortrix mokasen, Bitis arietans, Bitis caudalis, Bitis gabonica, Bitis g. rhinoceros, Bothrops asper, Bothrops alternata, Bothrops atrox, Bothrops cotiara, Bothrops jararaca, Bothrops newiedi, Bothrops medusa, Bothrops schlegli, Cerastes cerastes, Cerastes vipera, Crotalus adamanteus, C. atrox, C. basilicus, C. durissus totonatacus, C. h. horridus, C. m. molossus, C. ruber, C. scutalatus, C. v. cereberus, C. v. helleri, C. v. lutosus, C. v. oreganus, Echis carinatus sochurecki, Eristicophis macmahoni, Pseudocerastes persicus, Sistrurus m. barbouri, Sistrurus c. tergeminus, Trimeresurus flavoviridis, Trimeresurus gramineus, Vipera lebetina, Vipera ammondytes, Vipera palastinae,* and *Vipera r. russelli.*

The purified platelet adhesion inhibitors of the invention are then sequenced using standard procedures. The entire peptide may be sequenced, generally following reduction and alkylation of the cysteine residues in the native protein, which permits separation of individual subunits. Individual subunits can be proteolytically digested to generate fragments which are separated using RPLC and their protein sequences determined using automated protein sequenators such as Applied Biosystems 473A Protein Sequenator.

Alternatively, the entire sequence of the protein may be determined by retrieving DNA encoding the antiadhesive from cloned snake tissue DNA libraries. A variety of methods are known to obtain such DNAs, including screening with oligonucleotide probes designed on the basis of partial amino acid sequences for the antiadhesives or expression screening using antibodies prepared to the purified antiadhesives.

Recombinant and other Synthetic Production

The platelet antiadhesives (PAA) of the invention can be produced in a variety of ways, including using recombinant methods.

The genes encoding native PAA or mutants thereof can then be manipulated and expressed using a variety of recombinant systems. Host systems which do not process the translated protein can be used provided there is proper design of the expression system. For example, the expression system is constructed by placing an ATG start codon immediately preceding the desired N-terminus and a termination codon after the desired C-terminus, with appropriate modification of any adjacent sequences. The desired coding sequence is then ligated in operable linkage to a control system functional in procaryotic or eucaryotic hosts, as desired. A large number of control systems are now known in the art.

If processing of the PAA is desired, certain eucaryotic systems may be advantageous. Attention should be paid to the choice of the recombinant host, which choice will determine the nature of the processing. It is also possible to prevent processing by modification of the gene sequence so as to encode substitute amino acids in positions believed to be susceptible to cleavage or glycosylation by proteolytic or glycosylating enzymes. For example, arginine or lysine could be replaced by threonine residues, thus rendering the resulting peptide non-susceptible to trypsin cleavage at those sites. In the alternative, expression can be effected in hosts which are deficient in enzymes capable of processing these peptides.

As the genes encoding the PAA are made obtainable by the availability of the probes constructed from PAA-encoding DNA or by the availability of anti PAA antibodies, these genes can be manipulated by replacing the codons for one or more amino acids by site directed mutagenesis, to obtain sequences encoding analogs of these peptides which retain PAA activity.

Construction of expression vectors and recombinant production of the appropriate DNA sequences are performed by methods known in the art per se.

Expression can be in procaryotic or eucaryotic systems. Procaryotes most frequently are represented by various strains of *E. coli*. However, other microbial strains may also be used, such as bacilli, for example *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species or pUC series vectors. Commonly used procaryotic control sequences, which are defined herein to include promoters for transcription initiation, optionally with an operator, along with ribosome binding site sequences, including such commonly used promoters as the beta-lactamase (penicillinase) and lactose (lac) promoter systems, the tryptophan (trp) promoter system and the lambda-derived $P_L$ promoter system compatible with procaryotes can be used.

The expression systems useful in the eucaryotic hosts comprise promoters derived from appropriate eucaryotic genes. A class of promoters useful in yeast, for example, include promoters for synthesis of glycolytic enzymes, including those for 3-phosphoglycerate kinase. Other promoters include those from the enolase gene or the Leu2 gene obtained from YEp13.

Suitable mammalian promoters include the metallothionein promoter, the early and late promoters from SV40 or other viral promoters such as those derived from polyoma, adenovirus II, bovine papilloma virus or avian sarcoma viruses. Suitable viral and mammalian enhancers can also be used. In the event plant cells are used as an expression system, the nopaline synthesis promoter is appropriate. Insect cells may also be used as hosts in conjunction with the bacculovirus-based expression system.

The expression system is constructed from the foregoing control elements operably linked to the PAA encoding sequences using standard methods, employing standard ligation and restriction techniques which are well understood in the art. Isolated plasmids, DNA sequences, or synthesized oligonucleotides are cleaved, tailored, and religated in the form desired.

The constructed vector is then transformed into a suitable host. Depending on the host cell used, transformation is done using standard techniques appropriate to such cells. The transformed cells are then cultured under conditions favoring expression of the PAA encoding sequence and the recombinantly produced protein recovered from the culture.

In addition to recombinant production, peptides whose deduced sequences are sufficiently short to make direct peptide synthesis practical can be prepared using standard solid-phase techniques.

Thus, compounds within the scope of the present invention can be synthesized chemically by means well known in the art such as, e.g., solid-phase peptide synthesis. The synthesis is commenced from the carboxy-terminal end of the peptide using an alpha-amino protected amino acid. t-Butyloxycarbonyl (Boc) protective groups can be used for all amino groups even though other protective groups are suitable. For example, Boc—Val—OH, Boc—Leu—OH, Boc—Arg—OH or Boc—Tyr—OH (i.e., selected BNP analog carboxy-terminal amino acids) can be esterified to chloromethylated polystyrene resin supports. The polystyrene resin support is preferably a copolymer of styrene with about 0.5 to 2% divinyl benzene as a cross-linking agent which causes the polystyrene polymer to be completely insoluble in certain organic solvents. See Stewart, et al., *Solid-Phase Peptide Synthesis*, (1969), W. H. Freemen Co., San Francisco, and Merrifield, *J Am Chem Soc* (1963) 85:2149–2154. These and other methods of peptide synthesis are also exemplified by U.S. Pat. Nos. 3,862,925; 3,842, 067; 3,972,859; and 4,105,602.

The synthesis may use manual techniques or automatically employing, for example, an Applied Biosystems 430A or 431A Peptide Synthesizer (Foster City, Calif.) following the instructions provided in the instruction manual supplied by the manufacturer.

Of course, since automated synthesis also permits control of the sequence, the above-mentioned modifications to the amino acid sequence obtained by modifying the gene as described above are available using this method of synthesis. In addition, it is not necessary that the substituted amino acid be encoded by a gene. Therefore, the D-forms or beta-amino acids can be substituted for those natively present.

Preparation of Antibodies to the Antiadhesives

The invention platelet antiadhesives can also be utilized in immunization protocols to obtain antisera immunospecific for the invention compounds. The resulting PAA compounds can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures, now standard in the art, employing the invention compounds as antigens.

The antisera obtained can be used directly or monoclonal antibodies may be obtained by harvesting the peripheral blood lymphocytes or the spleen of the immunized animal and immortalizing the antibody-producing cells, followed by identifying the suitable antibody producers using standard immunoassay techniques.

Any of the invention compounds that are relatively small haptens are advantageously coupled to antigenically neutral carriers such as the conventionally used keyhole limpet hemocyanin (KLH) or serum albumin carriers. Coupling to carrier can be done by methods generally known in the art. Coupling can be done using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill.

Administration and Utility

The platelet adhesion inhibitors are useful therapeutically to prevent platelet adherence and thrombus formation and to prevent restenosis of arteries following invasive procedures such as angioplasty. Indications appropriate for such treatment include, without limitation, atherosclerosis and arteriosclerosis, acute myocardial infarction, chronic unstable angina, transient ischemic attacks and strokes, peripheral vascular disease, arterial thrombosis, preeclampsia, embolism, restenosis and/or thrombosis following angioplasty, carotid endarterectomy, anastomosis of vascular grafts, and chronic cardiovascular devices (e.g., in-dwelling catheters or shunts "extracorporeal circulating devices"). These syndromes represent a variety of stenotic and occlusive vascular disorders thought to be initiated by platelet adherence followed by activation of platelets, release of platelet granule contents which include potent growth factor which may be responsible for vascular smooth muscle proliferation in the neointimal layer of the vessel wall leading to restenosis, and subsequent platelet thrombus formation on damaged arterial vessel walls.

The platelet adhesion inhibitors may be used for prevention or abortion of arterial thrombus formation, in unstable angina and arterial emboli or thrombosis, as well as treatment or prevention of myocardial infarction (MI) and mural thrombus formation post-MI. They may be coadministered with thrombolytic agents such as streptokinase or plasminogen activators in order to inhibit platelet adherence and subsequent reocclusion of arteries.

In addition these antithrombotics can be used to suppress thrombosis and restenosis resulting from organ transplantations and can thus be used to prevent thrombosis-mediated organ rejection and transplant-induced atherosclerosis.

The platelet adhesion inhibitor dosage can range broadly depending upon the desired effects and the therapeutic setting. Typically, dosages will be about 0.001 and 10 mg/kg of the body weight of the individual. Administration is preferably parenteral, such as intravenous on a daily basis, for up to a week or as much as one or two months or more, which will vary dependent on the therapeutic regimen. If peptide fragments of the platelet adhesion inhibitor are used, other routes of administration can be utilized, such as intranasally, sublingually, or the like.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride or the like. In addition, if desired, the injectable pharmaceutical compositions may contain minor amounts of nontoxic auxiliary substances, such as wetting agents, pH buffering agents, and the like. If desired, absorption-enhancing preparations (e.g., liposomes) may be utilized.

The following examples are intended to illustrate, but not to limit, the invention.

EXAMPLE 1

Identification of Platelet Antiadhesive-Containing Snake Venom

For the assay, purified human vWF was prepared from human plasma cryoprecipitate using the procedure of Thorell et al., (supra) and formaldehyde-fixed washed platelets were prepared and assayed as described by Brinkhous and Read, (supra). Ristocetin (1.5 mg/ml final concentration) or botrocetin (10 μg/ml final concentration) were used to initiate platelet agglutination.

Seventy-three crude, lyophilized snake venoms obtained from either Sigma Chemical Company (St. Louis, Mo.) or Miami Serpentarium Labs (Salt Lake City, Utah) dissolved in distilled H₂O at a concentration of 10 mg/ml were subjected to preparative ultrafiltration using Centricon-10 and Centricon-30 (YM Membrane) microconcentrators (Amicon, Danvers, Mass.). Both filtrates (10 and 50 µl samples) and retentates (10 and 50 µl samples) were used as test samples in the platelet agglutination assay utilizing the prepared fixed-washed platelets with purified vWF. Inhibitory activity was only found in retentate samples from the Centricon-10 and -30 ultrafiltrations. The results are shown in Table 1.

TABLE 1

Snake Venoms Screened for Anti-GP Ib Activity
(Centricon-30 Retentates)

| | Activity |
|---|---|
| Elapidae | |
| Bungarus caerulus | − |
| Bungarus fasciatus | − |
| Dendroaspis jamesoni | − |
| Naja naja | − |
| Naja melanoleuca | − |
| Notechis scutatus scutatus | − |
| Ophiophagus hannah | − |
| Pseudechis porphyriacus | − |
| Pseudonaja textilis textilis | − |
| Tropidechis carinatus | − |
| Viperinae | |
| Bitis arietans | + |
| Bitis caudalis | + |
| Bitis gabonica | + |
| Bitis g. rhinoceros | + |
| Bitis nasicornus | − |
| Causus rhombeatus | − |
| Cerastes cerastes | + |
| Cerastes vipera | + |
| Echis carinatus sochurecki | + |
| Echis carinatus leakyi | + |
| Eristicophis macmahoni | + |
| Hypnale hypnale | + |
| Pseudocerastes persicus | + |
| Vipera ammodytes | + |
| Vipera aspis | − |
| Vipera berus | − |
| Vipera lebetina | + |
| Vipera palastinae | + |
| Vipera r. russelli | + |
| Crotalinae | |
| Agkistrodon acutus | + |
| Agkistrodon bilineatus | − |
| Agkistrodon c. contortrix | − |
| Agkistrodon c. laticinctus | − |
| Agkistrodon c. mokasen | + |
| Agkistrodon h. blomhoffi | + |
| Agkistrodon p. leucostoma | − |
| Agkistrodon p. piscivorous | − |
| Agkistrodon rhodostoma | − |
| Bothrops atrox | + |
| Bothrops asper | + |
| Bothrops alternatus | + |
| Bothrops cotiara | + |
| Bothrops jararaca | + |
| Bothrops lansbergi | − |
| Bothrops medusa | + |
| Bothrops nasuta | − |
| Bothrops newiedi | + |
| Bothrops pradoi | − |
| Bothrops schlegli | + |
| Crotalus adamanteus | + |
| Crotalus atrox | + |
| Crotalus basilicus | + |
| Crotalus cerastes | + |
| Crotalus d. durrisus | + |
| Crotalus d. totonatacus | + |

TABLE 1-continued

Snake Venoms Screened for Anti-GP Ib Activity
(Centricon-30 Retentates)

| | Activity |
|---|---|
| Crotalus d. terrificus | − |
| Croatlus h. horridus | + |
| Crotalus m. molossus | + |
| Crotalus r. ruber | + |
| Crotalus scutalatus | + |
| Crotalus v. cereberus | + |
| Crotalus v. concolor | − |
| Crotalus v. helleri | + |
| Crotalus v. lutosus | + |
| Crotalus v. oreganus | + |
| Crotalus v. viridis | + |
| Sistrurus c. tergeminus | + |
| Sistrurus m. barbouri | + |
| Trimeresures albolabris | + |
| Trimeresurus elegans | + |
| Trimeresurus flavoviridis | + |
| Trimeresurus gramineus | + |
| Trimeresurus purpureomaculatus | + |
| Trimeresurus wagleri | − |

The antiadhesion activity is present in some but not all species of Viperinae and Crotalinae, but absent in all species of Elapidae tested.

EXAMPLE 2

Purification of Platelet Antiadhesive From *Crotalus horridus horridus* Venom

A solution of 500 mg of *Crotalus horridus horridus* venom (Miami Serpentarium Labs, Lot #CH18SZ) in 7.0 ml of 0.5M acetic acid was applied to a column of Sephadex G-50 (fine) (Pharmacia, 2.5×100 cm) equilibrated and eluted with 0.5M acetic acid. The column was eluted at a flow rate of 25 ml/hr with 5 ml fractions being collected. Ten µl of each fraction was pooled in groups of 10 fractions (i.e., fractions 1–10, 11–20, 21–30, etc.) and lyophilized for analysis. The freeze-dried fractions were resuspended in 500 µl of distilled water and aliquots assayed for inhibitory activity in ristocetin induced platelet agglutination of fixed washed platelets reconstituted with purified vWF. Active inhibitory fractions in this assay (31–40) were pooled and lyophilized to obtain 95 mg of a white amorphous powder.

This material was dissolved in 5 ml of 0.01M NH₄OAc, pH 4.5 and applied to a Carboxymethyl-sephacyl column (2.2×13 cm) equilibrated in 0.01M to 0.5M NH₄OAc, to pH 6.5 was run and fractions (12 ml) were collected. The column was monitored at 254 nm/1.0 AUFS to identify fraction with UV absorbance (FIG. 1). UV absorbing fractions were individually lyophilized (20 µl each), resuspended in 1 ml of distilled H₂O and assayed for their ability to inhibit platelet agglutination. Fractions 13 through 17 displayed inhibitory activity and were individually lyophilized from H₂O three times to remove excess NH₄OAc.

Figure 2:
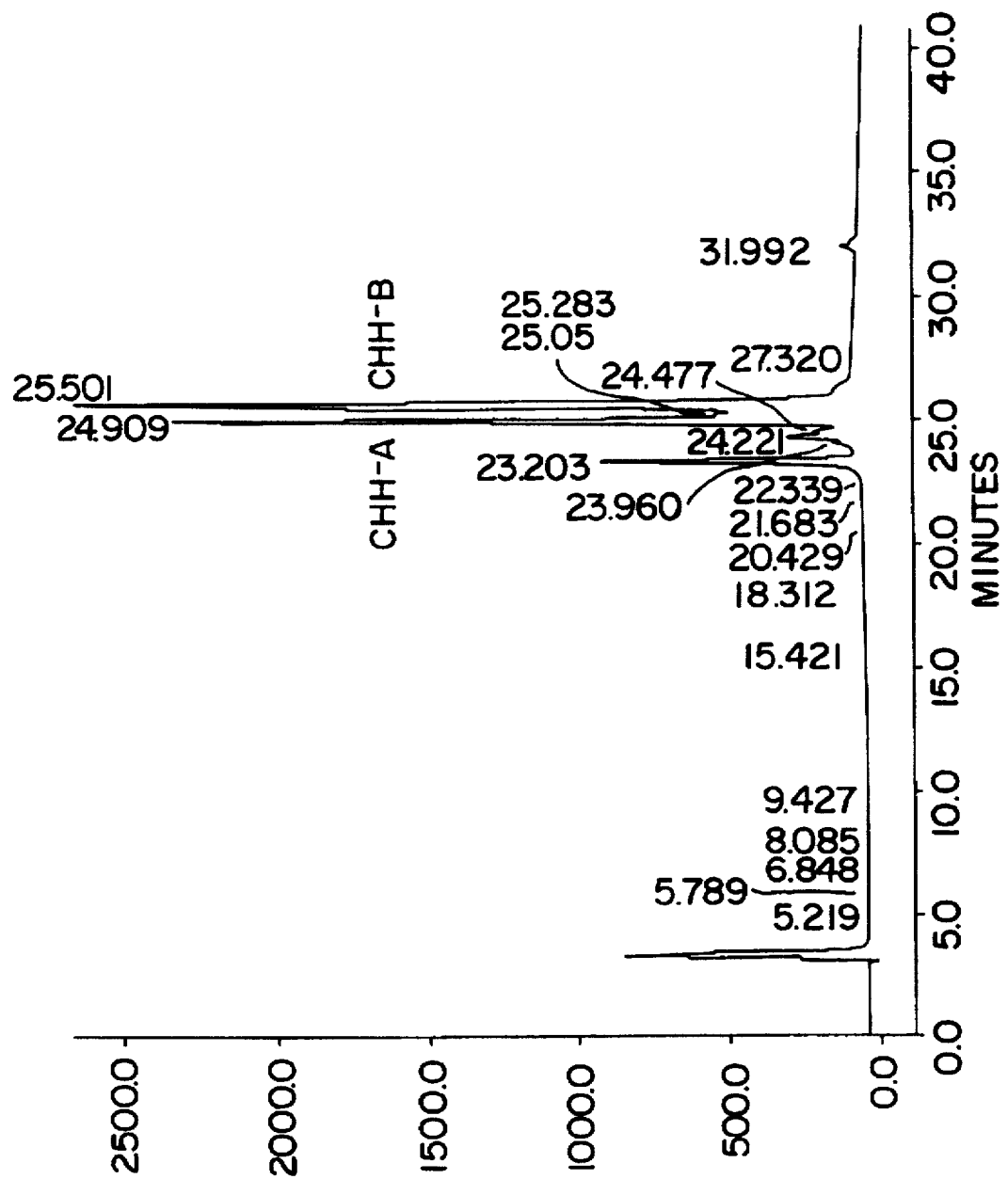
FIG. 2 shows active fractions from ion-exchange purification of CHH GPIb inhibitor analyzed on RPLC ($C_4$, acetonitrile/TFA gradient elution) monitored at 214 nm.
Figure 3A:
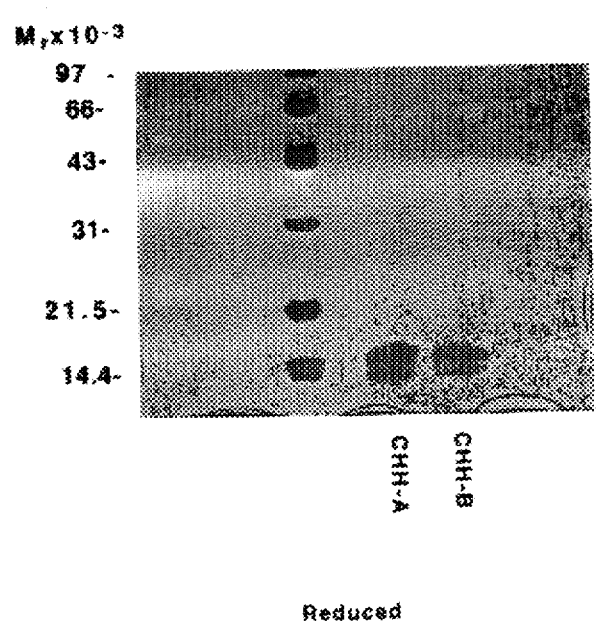
FIGS. 3A and 3B show results of SDS-PAGE performed on the active fractions of FIG. 2.
Figure 3B:
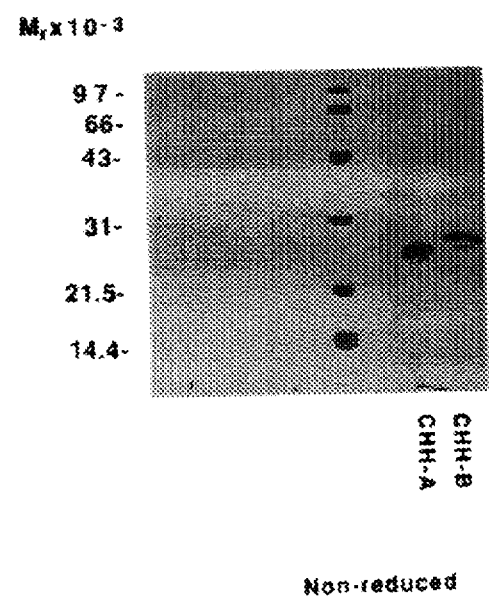

Analysis of the peak inhibitory fractions by SDS-polyacrylamide gel electrophoresis (non-reducing) revealed two major proteins that migrated with $M_r$=23–28 kd. Analysis of these fractions (100 µg) using analytical reversed-phase C₄ liquid chromatography (Vydac 214TP54, 0.46×25 cm, 1.0 ml/min flow, 300A, gradient elution from 15% acetonitrile/0.1% trifluoroacetic acid (TFA) to 70% acetonitrile in 30 min) revealed two major UV (214 nm) absorbing peaks (FIG. 2), which were collected and dried. Reanalysis of these two peaks by SDS-PAGE revealed that the earlier HPLC eluting peak, termed CHH-A, (24.9 min)

migrated at $M_r$=23 kd and the later eluting peak, termed CHH-B (25.6 min) migrated at $M_r$=25 kd (FIG. 3). Under reducing SDS-PAGE, CHH-A and CHH-B collapsed to two distinct protein chains $M_r$=12–15 kd. Native CHH-A and CHH-B were both able to inhibit botrocetin and ristocetin induced platelet agglutination in the washed system and also in platelet rich plasma to the same degree.

Figure 4:
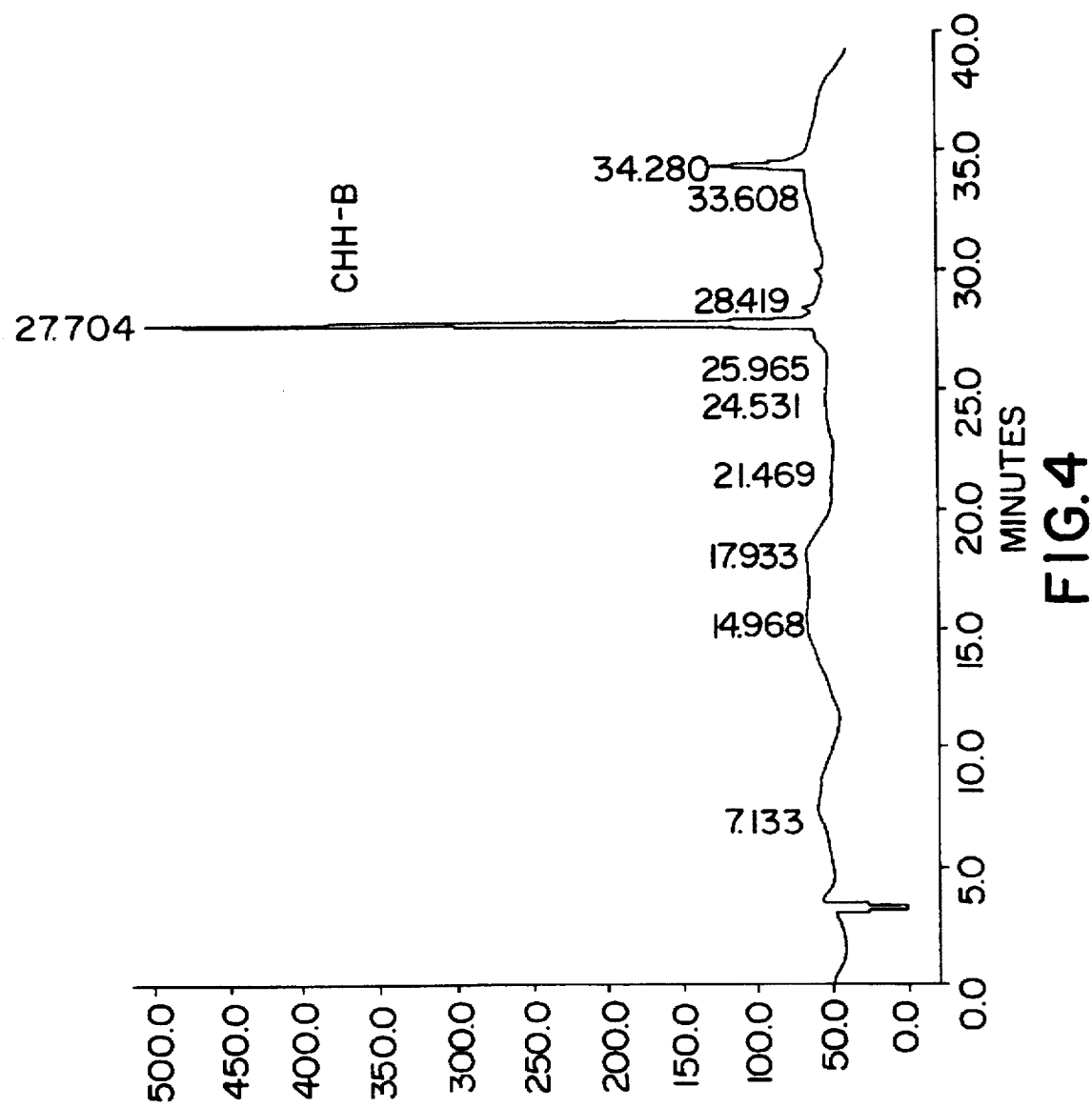
FIG. 4 shows the RPLC chromatogram of purified CHH-B on a $C_4$ column.
Figure 5:
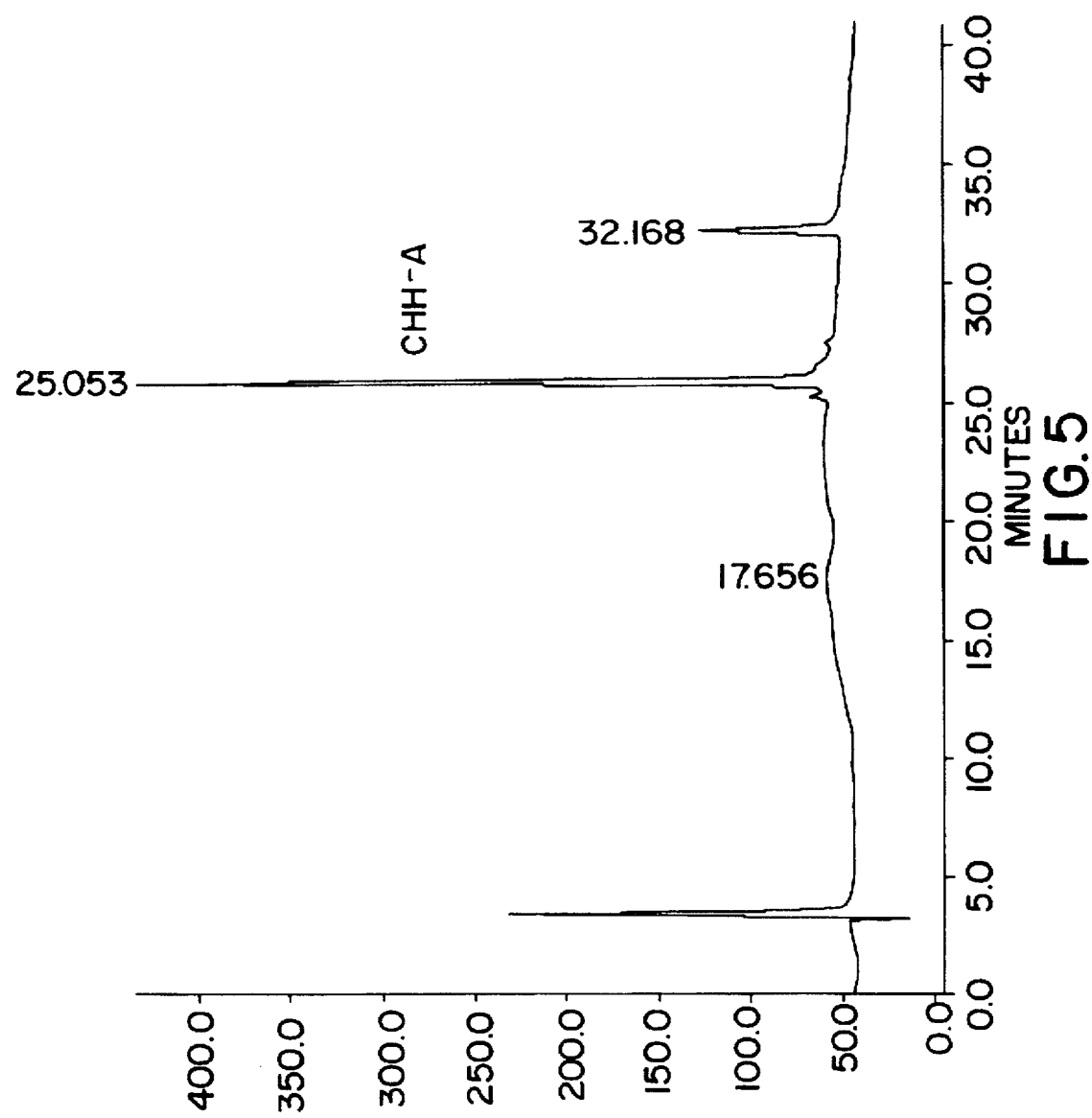
FIG. 5 shows the RPLC chromatogram of purified CHH-A on a $C_4$ column.

Preparative purification of CHH-A and CHH-B from the ion-exchange fractions was accomplished on a semi-preparative $C_4$ (214TP510, 3.5 ml/min) column using the same gradient elution conditions as the analytical analysis. FIG. 4 shows the analytical $C_4$ HPLC chromatogram of purified CHH-B and FIG. 5 shows the chromatogram for CHH-A. (The peak at 34 min in each figure is an artifact).

A portion of the purified protein (CHH-B) was reduced and alkylated (6M guanidine.HCl, 0.25M Tris-HCl, 20 mM EDTA, containing 20 mM dithiothreitol (DTT), pH 7.5, 8 hr 25° C. Excess iodoacetamide was added to the reduced protein for 8 hr at room temperature. The reduced and alkylated chains were separated from each other using $C_4$ reversed-phase HPLC. The earlier eluting subunit (CHH-B-β) and later eluting subunit (CHH-B-α) were individually submitted to N-terminal sequence analysis (Edman degradation) using an Applied Biosystem 473A protein sequenator.

The following N-terminal amino acid sequence was obtained for 37 cycles of Edman degradation for CHH-B-α=Asp-Leu-Glu-Cys-Pro-Ser-Gly-Trp-Ser-Ser-Tyr-Asp-Arg-Tyr-Cys-Tyr-Lys-Pro-Phe-Lys-Gln-Glu-Met-Thr-Trp-Ala-Asp-Ala-Glu-Arg-Phe-Cys-Ser-Glu-Gln-Ala-Lys (position 1 to position 37 of SEQ ID NO:). The complete amino acid sequence for this chain which contains 127 amino acids is shown in FIG. 6A.

The following fragments of CHH-B-α are disclosed, and denoted by the positions of the N-terminal and C-terminal residues inclusive in the CHH-B-α sequence shown in FIG. 6A: 1–17; 21–37; 78–109; 121–126; 18–20; 111–122; 1–111; 27–73; 92–101; 112–128; 12–26; 101–110; 101–127; 50–62; 88–106; and 63–87.

The following N-terminal amino acid sequence was obtained for 27 cycles for CHH-B-β: position 1 to position 29 of SEQ ID NO: 2). The complete amino acid sequence for this chain in shown in FIG. 6B.

The following fragments of CHH-B-β are disclosed, and denoted by the positions of the N-terminal and C-terminal residues inclusive in the CHH-B-β sequence shown in FIG. 6B: 1–44; 1–10; 28–46; 71–89; 92–117; 11–20; 48–80; 49–57; 66–69; 78–98; 58–65; 99–117; 1–24; 39–56; 85–109; and 110–117.

Figure 7:
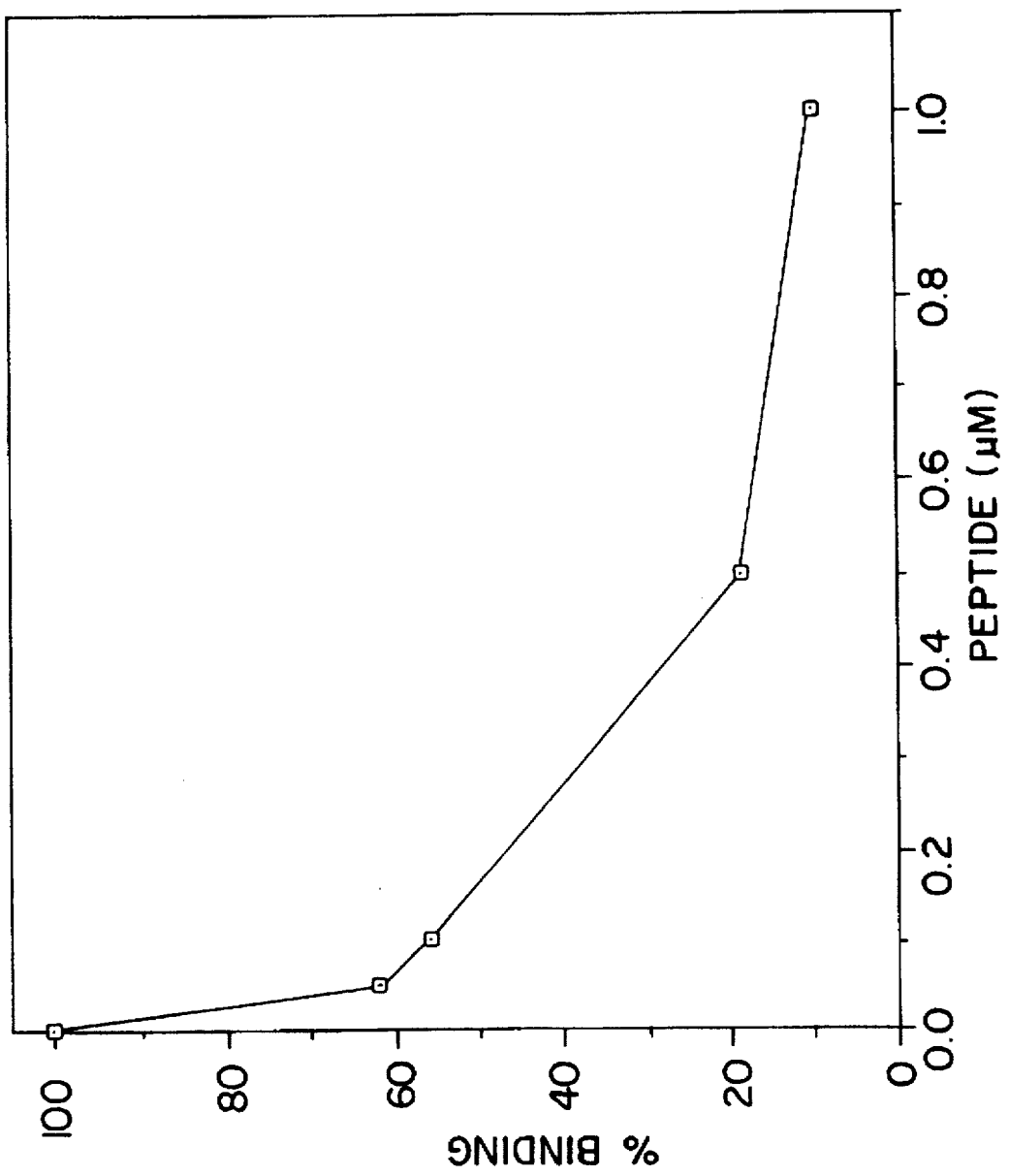
FIG. 7 shows the dose dependent inhibition of $^{125}$I-von Willebrand factor binding to fixed-washed platelets induced by botrocetin by CHH-B GPIb inhibitor.

The purified peptide CHH-B was tested in the vWF-platelet binding assay as performed according to the procedure of Ruggeri, et al. (supra). The results are shown in FIG. 7. Binding inhibition is dose dependent and concentrations of pure CHH-B at less than 200 nM inhibited the binding of vWF to the washed platelets.

EXAMPLE 2

Purification of Antiadhesive From the Venom of *Cerastes cerastes*

A solution of 500 mg of *Cerastes cerastes* venom (Miami Serpentarium Labs, Lot #CC12SZ in 5.0 ml of 0.5M acetic acid was applied to a column of Sephadex G-50 (fine) (Pharmacia, 2.5×100 cm) equilibrated and eluted with 0.5M acetic acid. The column run at a flow rate of 40 ml/hr with 8 ml fractions collected into polypropylene tubes. Twenty five μl of each fraction was pooled in groups of 10 fractions (1–10, 11–20, 21–30, etc.) and lyophilized. Freeze-dried fractions were resuspended in 100 μl of distilled water and aliquots assayed for inhibitory activity in ristocetin induced platelet agglutination of fixed-washed platelets reconstituted with purified vWF. Active fraction in this assay (fractions 21–40) were pooled and lyophilized to obtain 198 mg of a white powder.

This material was dissolved in 10 ml of 0.01M $NH_4OAc$, pH 4.5 and applied to a CM-sepharose column (2.2×13 cm). A pH and salt gradient running from 0.01M to 0.5M $NH_4OAc$, to pH 6.5 was run and fractions (10 ml) collected into polypropylene tubes. The column effluent was monitored at 254 nm/1.0 AUFS to identify fractions with UV absorbance. Fractions were again pooled with 25 μl from each fraction into groups of 10 fractions and lyophilized. The fractions were redissolved in 100 μl of distilled $H_2O$ and assayed for their ability to inhibit platelet agglutination. Fractions 81–100 displayed inhibitory activity which were pooled and lyophilized from $H_2O$ three times to remove excess $NH_4OAc$.

Analysis of the inhibitory fractions by SDS-PAGE (non-reducing) revealed one major protein band which stained that migrated with $M_r$=23–28 kd. Under reducing SDS-PAGE, the native protein collapsed to two distinct protein chains $M_r$=12–15 kd. Analysis of the fractions on analytical $C_4$ reversed-phase liquid chromatography (Vydac 214TP54, 0.46×25 cm, 1.0 ml/min flow, 300A) gradient elution from 30% acetonitrile/0.1% TFA to 70% acetonitrile in 30 min revealed one major UV (214 nm) absorbing peak as shown in FIG. 8 (the peaks at 27 and 31 min are artifacts).

A portion of the purified protein (CC) was reduced and alkylated with iodoacetamide as in Example 1. The carboxyamidomethylated chains were separated using a reversed-phase Vydac-Phenyl column. The earlier eluting subunit (CC-β) and later eluting subunit (CC-α) were individually submitted to N-terminal sequence analysis using the Applied Biosystems 473A protein sequenator.

The following N-terminal amino acid sequence was obtained for 25 cycles of Edman degradation for CC-β: Leu-Asp-Cys-Pro-Leu-Asp-Ser-Ser-Xaa-His-Glu-Glu-Lys-Cys-Tyr-Lys-Val-Phe-Phe-Leu-Leu-Xaa-Thr-Trp-Glu (SEQ ID NO: 3).

The following N-terminal amino acid sequence was obtained for 20 cycles for CC-α: Asp-Gln-Asp-Cys-Leu-Pro-Gly-Trp-Ser-Tyr-Tyr-Glu-Lys-Tyr-Cys-Tyr-Lys-Val-Phe-Glu (SEQ ID NO:4).

EXAMPLE 4

Purification of Antiadhesive From the Venom of *Pseudocerastes persicus*

A solution of 1000 mg of *Pseudocerastes persicus* venom (Miami Serpentarium Labs, Lot #PS8SZ) in 7.0 ml of 0.5M acetic acid was applied to a column of Sephadex G-50f (Pharmacia, 2.5×100 cm), eluted and assayed as described in Examples 2 and 3. Fractions which were active (Fractions 31–50) were pooled and lyophilized.

Approximately 160 mg of this material was adsorbed and gradient-eluted from a CM-Sepharose column (2.2×13 cm) using an $NH_4OAc$ buffer running from 0.01M to 0.5M $NH_4OAc$. Active fractions (6 ml each, Fractions 64–72) were found to be active in the fixed-platelet assay, pooled and lyophilized from water several times to remove the volatile salt.

Final purification was effected by semipreparative $C_4$ reversed-phase liquid chromatography employing a gradient of acetonitrile in 0.1% TFA which ran from 15–70% acetonitrile in 30 minutes. A portion of the material (300 µg) was reduced and carboxyamidomethylated as described in Example 2. The carboxyamidomethylated chains were separated on $C_4$ RPLC as described and the individual chains submitted to N-terminal sequence analysis.

The earlier eluting subunit, PP-β, was subjected to Edman degradation for 50 cycles to obtain the following sequence: Asp-Cys-Pro-Ser-Asp-Trp-Ser-Ser-His-Glu-Gly-His-Cys-Tyr-Lys-Val-Phe-Asn-Leu-Tyr-Lys-Thr-Trp-Glu-Asp-Ala-Glu-Lys-Phe-Cys-Thr-Glu-Gln-Ala-Asn-Gly-Gly-His-Leu-Val-Ser-Ile-Asp-Ser-Lys-Lys-Glu-Ala-Asn-Phe (SEQ ID NO:5).

The following amino acid sequence was determined for 31 cycles of the PP-α chain: Ala-Leu-Asn-Cys-Ala-Ser-Gly-Trp-Ser-Ala-Tyr-Asp-Gln-His-Cys-Tyr-Lys-Ala-Phe-Asp-Glu-Pro-Lys-Ser-Trp-Ala-Asp-Asp-Glu-Lys-Phe (SEQ ID NO: 6).

EXAMPLE 5

Purification of Platelet Antiadhesive From *Vipera r. russelli* Venom

Using the methods of Examples 2–4, 1 gram of venom from *Vipera r. russelli* was purified to yield the GPIb inhibitor RV. A portion of the purified inhibitor was carboxyamidomethylated as described in Examples 2–4, and the subunits separated with $C_4$ RPLC.

N-terminal sequencing of the later eluting subunit for 22 cycles revealed the following amino acid sequence: Gly-Phe-Ser-Cys-Pro-Asn-Gly-Trp-Ser-Ser-Phe-Gly-Arg-Tyr-Cys-Tyr-Lys-Pro-Ile-Glu-Pro-Leu (SEQ ID NO:7).

EXAMPLE 6

Inhibition of Botrocetin/Ristocetin-Induced Agglutination

Figure 9A:
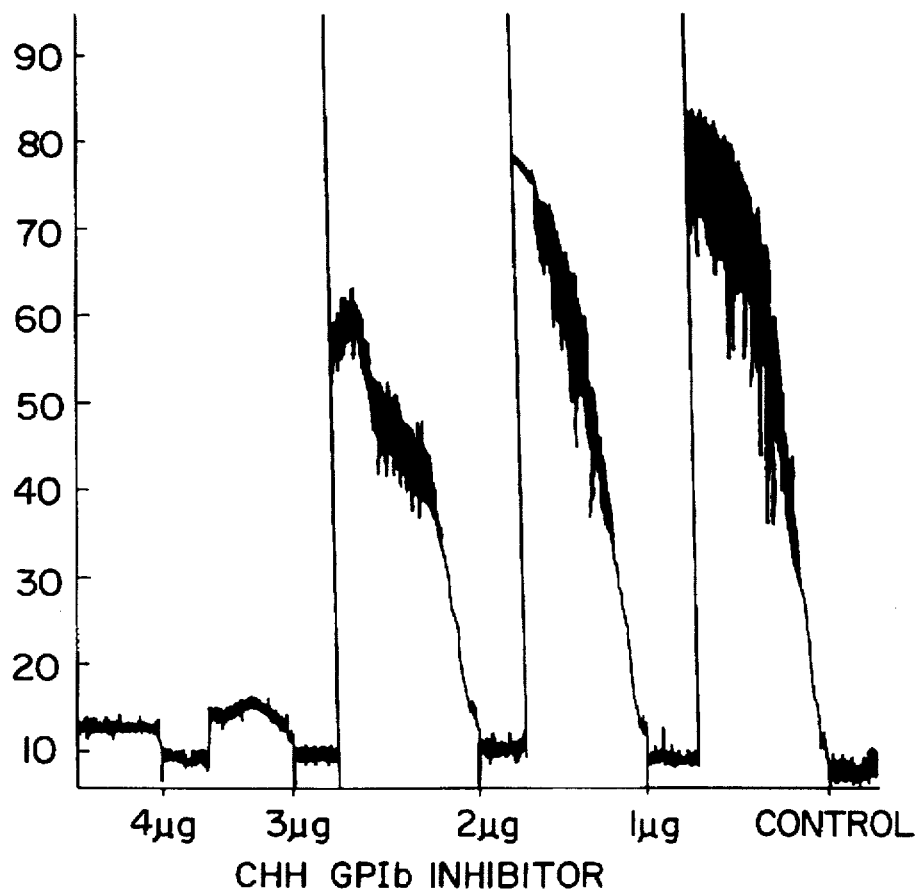
FIG. 9A shows the dose dependent inhibition of ristocetin-induced platelet agglutination by purified *Crotalus h. horridus* antiadhesive in PRP.
Figure 9B:
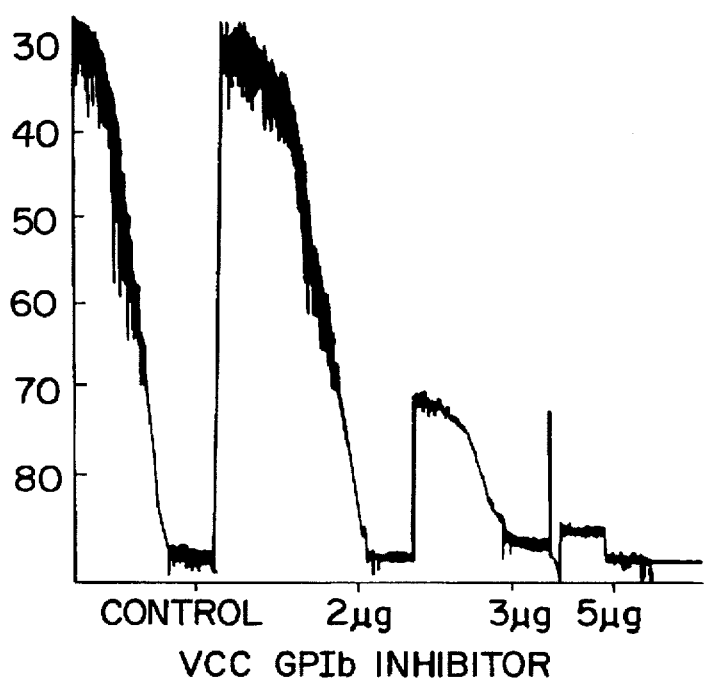
FIG. 9B shows and the dose dependent inhibition of agglutination by *Cerastes cerastes* antiadhesive.

The purified proteins from *C. horridus horridus*, as prepared in Example 2, and from *C. cerastes*, as prepared in Example 3, were subjected to the botrocetin/ristocetin-induced agglutination inhibition assay using PRP, as described above. The results are shown in FIG. 9. Again, a dose dependent effect is shown, concentrations as low as 2–3 µg/ml are able to show inhibition.

---

I claim:

1. An isolated antibody immunospecific for a snake venom platelet antiadhesive peptide, said peptide inhibiting the binding of vWF to GPIb-IX receptors, but not binding of Fg to GPIIb-IIIa receptors in purified and isolated form, obtainable from a snake venom selected from the group consisting of: *Agkistrodon acutus, Agkistrodon halys blomhoffi, Agkistrodon contortrix mokasen, Bitis arietans, Bitis caudalis, Bitis gabonica, Bitis g. rhinoceros, Bothrops asper, Bothrops alternata, Bothrops atrox, Bothrops cotiara, Bothrops jararaca, Bothrops newiedi, Bothrops medusa, Bothrops schiegli, Cerastes cerastes, Cerastes vipera, Crotalus admanteus, C atrox, C basilicus, C. durissus totonatacus, C. h. horridus, C. m. molossus, C ruber, C. scutalatus, C. v. cereberus, C. v. helleri, C. v. lutosus, C v. oreganus, Echis carinatus sochurecki, Eristicophis macmahoni, Pseudocerastes persicus, Sistrurus m. barbouri, Sistrurus c. tergeminus, Trimeresurus flavoviridis, Trimeresurus gramineus, Vipera lebetina, Vipera ammondytes, Vipera palastinae, and Vipera r. russelli.*

2. The antibody of claim 1, wherein said platelet antiadhesive is isolated from a venom of a snake selected from the group consisting of *Cerastes cerastes, C. h. horridus, Vipera r. russeli* and *Pseudocerastes persicus.*

3. The antibody of claim 1, further characterized as being a monoclonal antibody.

4. A method of assaying for a platelet antiadhesive peptide, comprising the steps of providing a sample; contacting the sample with an antibody of claim 1, and screening the sample to determine whether said antibodies bind to the sample.

5. The antibody of claim 1 wherein the platelet antiadhesive is a heterodimer wherein one member of said heterodimer has a MW of about 14 kd and has the N-terminal sequence:

Asp-Leu-Glu-Cys-Pro-Ser-Gly-Trp-Ser-Ser-Tyr-Asp-Arg-Tyr-Cys-Tyr-Lys-Pro-Phe-Lys-Gln-Glu-Met-Thr-Trp-Ala-Asp-Ala-Glu-Arg-Phe-Cys-Ser-Glu-Gln-Ala-Lys (position 1 to position 37 of SEQ ID No: 1).

6. The antibody of claim 1 herein the platelet antiadhesive is a heterodimer wherein one member of said heterodimer has a MW of about 14 kd and has the N-terminal sequence:

Asp-Cys-Pro-Ser-Asp-Trp-Ser-Ser-Tyr-Glu-Gly-His-Cys-Tyr-Arg-Val-Phe-Gln-Gln-Glu-Met-Thr-Trp-Asp-Asp-Ala-Glu-Lys-Phe (position 1 to position 29 of SEQ ID No:2).

7. The antibody of claim 1 wherein the platelet antiadhesive is a heterodimer wherein one member of said heterodimer has a MW of about 14 kd and has the N-terminal sequence:

Leu-Asp-Cys-Pro-Leu-Asp-Ser-Ser-Xaa-His-Glu-Glu-Lys-Cys-Tyr-Lys-Val-Phe-Phe-Leu-Leu-Xaa-Thr-Trp-Glu-(Seq ID No:3).

8. The antibody of claim 1 wherein the platelet antiadhesive is a heterodimer wherein one member of said heterodimer has a MW of about 14 kd and has the N-terminal sequence:

Asp-Gln-Asp-Cys-Leu-Pro-Gly-Trp-Ser-Tyr-Tyr-Glu-Lys-Tyr-Cys-Tyr-Lys-Val-Phe-Glu (SEQ ID No:4).

9. The antibody of claim 1 wherein the platelet antiadhesive is a heterodimer wherein one member of said heterodimer has a MW of about 14 kd and has the N-terminal sequence:

Asp-Cys-Pro-Ser-Asp-Trp-Ser-Ser-His-Glu-Gly-His-Cys-Tyr-Lys-Val-Phe-Asn-Leu-Tyr-Lys-Thr-Trp-Glu-Asp-Ala-Glu-Lys-Phe-Cys-Thr-Glu-Gln-Ala-Asn-Gly-Gly-His-Leu-Val-Ser-Ile-Asp-Ser-Lys-Lys-Glu-Ala-Asn-Phe (SEQ ID No:5).

10. The antibody of claim 1 wherein the platelet antiadhesive is a heterodimer wherein one member of said heterodimer has a MW of about 14 kd and has the N-terminal sequence:

Ala-Leu-Asn-Cys-Ala-Ser-Gly-Trp-Ser-Ala-Tyr-Asp-Gln-His-Cys-Tyr-Lys-Ala-Phe-Asp-Phe-Asp-Glu-Pro-Lys-Ser-Trp-Ala-Asp-Asp-Glu-Lys-Phe (SEQ ID No:6).

11. The antibody of claim 1 wherein the platelet antiadhesive is a heterodimer wherein one member of said heterodimer has a MW of about 14 kd and has the N-terminal sequence:

Gly-Phe-Ser-Cys-Pro-Asn-Gly-Trp-Ser-Ser-Phe-Gly-Arg-Tyr-Cys-Tyr-Lys-Pro-Ile-Glu-Pro-Leu (SEQ ID No.7).

12. The antibody of claim 3, wherein said platelet antiadhesive is isolated from a venom of a snake selected from the group consisting of *Cerastes cerastes, C. h. horridus, Vipera r. russeli*, and *Pseudocerastes persicus*.

13. A method of assaying for a platelet antiadhesive peptide, comprising the steps of providing a sample; contacting the sample with an antibody of claim 3, and screening the sample to determine whether said antibodies bind to the sample.

14. The antibody of claim 3 wherein the platelet antiadhesive is a heterodimer wherein one member of said heterodimer has a MW of about 14 kd and has the N-terminal sequence:

Asp-Leu-Glu-Cys-Pro-Ser-Gly-Trp-Ser-Ser-Tyr-Asp-Arg-Tyr-Cys-Tyr-Lys-Pro-Phe-Lys-Gln-Glu-Met-Thr-Trp-Ala-Asp-Ala-Glu-Arg-Phe-Cys-Ser-Glu-Gln-Ala-Lys (position 1 to position 37 of SEQ ID No: 1).

15. The antibody of claim 3 wherein the platelet antiadhesive is a heterodimer wherein one member of said heterodimer has a MW of about 14 kd and has the N-terminal sequence:

Asp-Cys-Pro-Ser-Asp-Trp-Ser-Ser-Tyr-Glu-Gly-His-Cys-Tyr-Arg-Val-Phe-Gln-Gln Glu-Met-Thr-Trp-Asp-Asp-Ala-Glu-Lys-Phe (position 1 to position 29 of SEQ ID No:2).

16. The antibody of claim 3 wherein the platelet antiadhesive is a heterodimer wherein one member of said heterodimer has a MW of about 14 kd and has the N-terminal sequence:

Leu-Asp-Cys-Pro-Leu-Asp-Ser-Ser-Xaa-His-Glu-Glu-Lys-Cys-Tyr-Lys-Val-Phe-Phe-Leu-Leu-Xaa-Thr-Trp-Glu-(Seq ID No:3).

17. The antibody of claim 3 wherein the platelet antiadhesive is a heterodimer wherein one member of said heterodimer has a MW of about 14 kd and has the N-terminal sequence:

Asp-Gln-Asp-Cys-Leu-Pro-Gly-Trp-Ser-Tyr-Tyr-Glu-Lys-Tyr-Cys-Tyr-Lys-Val-Phe-Glu (SEQ ID No:4).

18. The antibody of claim 3 wherein the platelet antiadhesive is a heterodimer wherein one member of said heterodimer has a MW of about 14 kd and has the N-terminal sequence:

Asp-Cys-Pro-Ser-Asp-Trp-Ser-Ser-His-Glu-Gly-His-Cys-Tyr-Lys-Val-Phe-Asn-Leu-Tyr-Lys-Thr-Trp-Glu-Asp-Ala-Glu-Lys-Phe-Cys-Thr-Glu-Gln-Ala-Asn-Gly-Gly-His-Leu-Val-Ser-Ile-Asp-Ser-Lys-Lys-Glu-Ala-Asn-Phe (SEQ ID No:5).

19. The antibody of claim 3 wherein the platelet antiadhesive is a heterodimer wherein one member of said heterodimer has a MW of about 14 kd and has the N-terminal sequence:

Ala-Leu-Asn-Cys-Ala-Ser-Gly-Trp-Ser-Ala-Tyr-Asp-Gln-His-Cys-Tyr-Lys-Ala-Phe-Asp-Phe-Asp-Glu-Pro-Lys-Ser-Trp-Ala-Asp-Asp-Glu-Lys-Phe (SEQ ID No:6).

20. The antibody of claim 3 wherein the platelet antiadhesive is a heterodimer wherein one member of said heterodimer has a MW of about 14 kd and has the N-terminal sequence:

Gly-Phe-Ser-Cys-Pro-Asn-Gly-Trp-Ser-Ser-Phe-Gly-Arg-Tyr-Cys-Tyr-Lys-Pro-Ile-Glu-Pro-Leu (SEQ ID No.7).

* * * * *